United States Patent

DeAngelis et al.

[11] Patent Number: 5,973,008
[45] Date of Patent: Oct. 26, 1999

[54] METHOD FOR CONTROLLING TERMITES

[75] Inventors: Alan R. DeAngelis, Pennington; Jane A. Dybas, Flemington, both of N.J.; John A. Dixson, Newton, Pa.

[73] Assignee: FMC Corporation

[21] Appl. No.: 08/844,213

[22] Filed: Apr. 18, 1997

Related U.S. Application Data

[60] Provisional application No. 60/016,627, May 1, 1996.

[51] Int. Cl.$^6$ .................................................. A01N 47/28
[52] U.S. Cl. ............................................................. 514/594
[58] Field of Search ............................................. 514/594

[56] References Cited

U.S. PATENT DOCUMENTS 4,170,657  10/1979  Rigterink .................................. 424/322
4,536,341  8/1985  Rigterink et al. ................. 260/453 AR
5,556,883  9/1996  Thomas et al. .......................... 514/594

FOREIGN PATENT DOCUMENTS

85/01047  3/1985  WIPO .

OTHER PUBLICATIONS

Tomlin, The Pesticide Manual, 10$^{th}$ Ed. pp. 1023–1024 (1995).
Tomlin, The Pesticide Manual, 10$^{th}$ Ed. (1995) pp. 283–284.

*Primary Examiner*—Allen Robinson
*Attorney, Agent, or Firm*—FMC Corporation

[57] ABSTRACT

The present invention relates to a method for controlling domestic pests using 2-chloro-N-[{(4'-chloro-2-methoxy[1,1'-biphenyl]4-yl)amino}carbonyl]benzamide. The benzamide is particularly effective against termites and is suitable for use in baits.

8 Claims, No Drawings

METHOD FOR CONTROLLING TERMITES

FIELD OF INVENTION

This application claims the benefit of the filing of U.S. Provisional Application 60/016,627 filed May 1, 1996.

The present invention relates to a method for controlling termites. More specifically the invention relates to the use of 2-chloro-N-[{(4'-chloro-2-methoxy[1,1'-biphenyl]4-yl)amino}carbonyl]benzamide and formulations thereof to control termites. Most specifically the invention relates to the use of the aforementioned composition to control termites by incorporation of the composition in a bait formulation.

BACKGROUND

Subterranean termites, which cause nearly a billion dollars in annual damage to U.S. homes, are difficult to control due to their large colonies and large foraging territories. The Formosan subterranean termite *Coptotermes formosanus* Shiraki and the eastern subterranean termite *Reticulitermes flavipes*, for example, each form colonies containing up to several million termites that can forage a linear distance of 79 to 100 meters (N.-Y. Su, J. Econ. Entomol. 87, 389–397, 1994).

A common method of protection for homes makes use of a barrier treatment to surround the home with a narrow, underground trench containing a termiticide. However, barrier treatments typically require the soil incorporation of a large amount of termiticide (5–10 kg for a single family home).

Termite baits have also been used in termite control, most effectively as part of an integrated pest management program. The bait itself is typically a piece of wood or other source of cellulose, such as cardboard. Upon finding a satisfactory bait, foraging termites will use trail pheromones to recruit others. A termite may also become exposed to the bait indirectly by oral transfer from another termite, a phenomenon known as trophallaxis. By a combination of recruitment and trophallaxis, the bait is eventually delivered to much of the colony over a period of a few days to several months. Because of the time necessary to disperse the bait throughout the colony, a toxicant mixed in the bait to control termites should be slow-acting.

In addition to their lethal effects, many termiticides are also termite repellents at varying concentrations (N.-Y. Su and R. H. Schreffrahn, J. Econ. Entomol., 86, 1453–1457, 1993). A suitable termiticide for use in a bait will therefore have lethal activity at concentrations well below those that cause repellency.

Insect growth regulators (IGRs) are attractive as bait toxicants because they are inherently slow-acting compounds. Examples of IGRs reported to have activity against termites include methoprene (isopropyl (2E-4E)-11-methoxy-3,7,11-trimethyl-2,4-dodecadienoate), pyriproxyfen (2-[1-methyl-2-(4-phenoxyphenoxy)ethoxy]pyridine), fenoxycarb (O-ethyl N-[2-(4-phenoxyphenoxy)ethylcarbamate), and hexaflumuron (N-[{(3,5-dichloro-4-(1,1,2,2-tetrafluoroethoxy)phenyl)amino}carbonyl]-2,6-difluorobenzamide). U.S. Pat. No. 5,300,293 describes a bait containing these compounds for controlling cockroaches and termites.

The IGR hexaflumuron is a highly active chitin synthesis inhibitor belonging to a class of compounds commonly known as the benzoylphenylureas. It is the active ingredient in DowElanco's Sentricon™ System for termite control and its activity has been reported in the literature (N.-Y. Su, J. Econ. Entomol., 87, 389–397,1994). Structurally related compounds having lethal activity against termites include chlorfluazuron, diflubenzuron, triflumuron and lufenuron.

International Publication Number WO 85/01047 discloses insecticidal activity against foliar feeding pests for compounds of the formula:

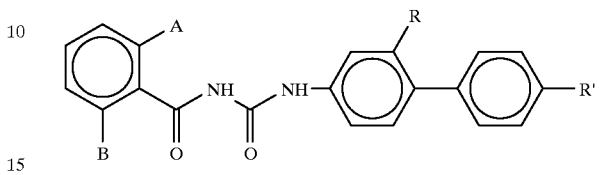

Specifically disclosed in the above reference is 2-chloro-N-[{(4'-chloro-2-methoxy[1,1'-biphenyl]4-yl)amino}carbonyl]benzamide (A). It has now been found that compound A is also highly effective against termites. In particular, it has now been found that compound A is termiticidal at very low concentrations and slow enough acting to be highly effective in a termite bait.

SUMMARY OF THE INVENTION

The use of 2-chloro-N-[{(4'-chloro-2-methoxy[1,1'-biphenyl]-4-yl)amino}carbonyl]-benzamide (A) to control termites is described.

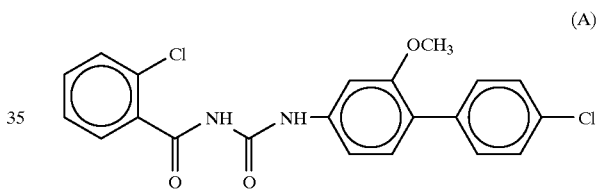

Compound A, shown above, is incorporated in a termite bait or composition or other suitable carrier. It is also useful in the control of the following domestic insect pests: cockroaches (*Blattella germanica*), *Periplaneta spp.*, fleas (*Ctenocephalides spp.*), ants, and flies (*Musca domestica*).

DISCLOSURE OF THE INVENTION

This invention describes the use of 2-chloro-N-[{(4'-chloro-2-methoxy[1,1'-biphenyl]4-yl)amino}carbonyl]benzamide (A) for controlling termites. It is surprisingly very active as a termiticide when compared to a recognized commercial standard. The composition of the present invention is also very slow acting by ingestion, does not exhibit fast acting contact activity which may prevent the spreading of bait to other termites, and may be transferred among termites by trophallaxis. Compound A may be incorporated in a termite bait or composition or other suitable carrier.

Compound A may be prepared by the method shown in the following schema:

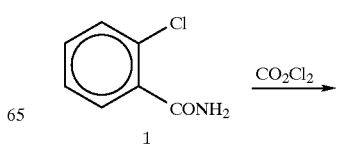

-continued

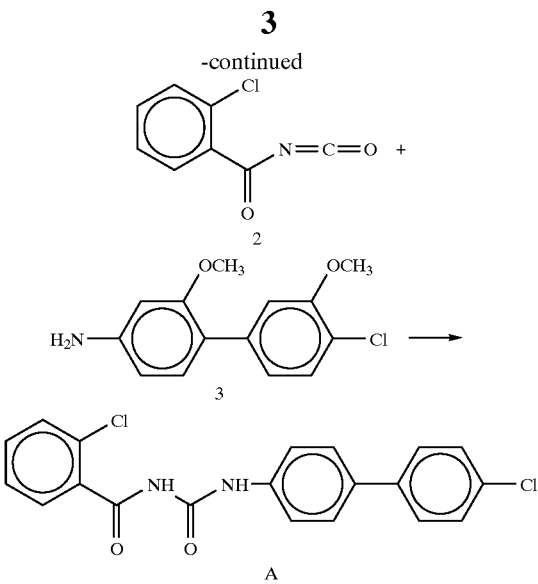

2-Chlorobenzamide (1) is heated with oxalyl chloride in methylene chloride to give the substituted benzoylisocyanate 2. Reaction of 2 with 4'-chloro-2-methoxybiphenyl amine (3) provides compound A. This general procedure was described by Wellinga, et al., J. Agr. Food Chem., 21, 348 (1973) as Methods A and B in J. Agr. Food Chem., 21, 993 (1973), both incorporated herein by reference.

The intermediate biphenylamine 3 may be prepared as described in International Publication Number WO 85/01047, incorporated herein by reference and shown in the following schema:

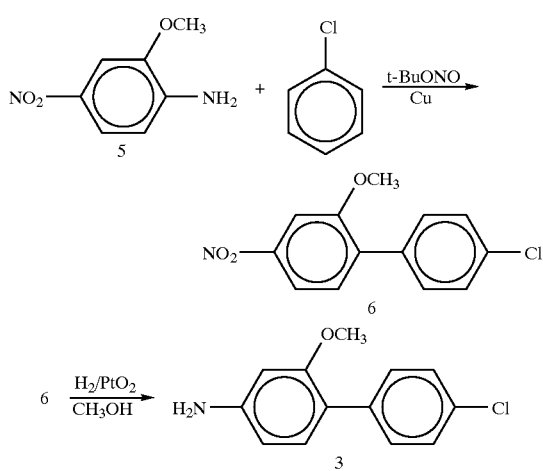

2-Methoxy4-nitroaniline 5 and chlorobenzene are heated in the presence of t-butylnitrite and copper powder to give 2-(4-chlorophenyl)-5-nitroanisole 6. Hydrogenation of 6 with platinum oxide in methanol (a base such as morpholine may be used) provides the desired biphenyl amine 3.

For obtaining the aryl-aryl coupling product 6, it should be noted that in recent years newer, more efficient methods have been developed for aryl-aryl couplings in general (R. B. Miller and S. Dugar, Organometallics, 3, 1263,1984 and N. Miyaura, T. Yanagi and A. Suzuki, Synth. Commun., 11(7), 513,1981). While these newer methods were not used herein to make the biphenyl intermediates leading to compound A of the present invention, they may provide a superior route to such intermediates.

The method of preparation is detailed in the following procedures.

EXAMPLE 1

Preparation of 2Chloro-N-[{(4'-chloro-2-methoxy [l1,1'-biphenyl]-4-yl)amino}carbonyl]benzamide (Compound A)

Step A 2-(4-Chlorophenyl -5-nitroanisole

To a stirred mixture of 2-methoxy-4-nitroaniline (29.8 g, 0.2 mole), chlorobenzene (1000 g, 8.8 mole) and copper powder (29.8 g) was added t-butylnitrite (27.6 g, 0.3 mole) over a thirty minute period. After complete addition the mixture was heated to 70–90° C. with stirring for four hours. The mixture was then allowed to stir at ambient temperature for 18 hours. After removing excess chlorobenzene by distillation the crude material was passed through a silica gel column using toluene. Product containing fractions were concentrated to give an oil that was chromatographed on a second silica gel column using 1:1 heptane/toluene to provide 26.0 g of an oil containing a mixture of isomers. Preparative gas chromatography gave pure 2-(4-chlorophenyl)-5-nitroanisole as shown by IR and NMR.

Step B 4-(4-Chlorophenyl)-3-methoxyaniline

Hydrogenation of 2-(4-chlorophenyl)-5-nitroanisole (0.6.g, 2.0 mmol) with platinum oxide (20 mg) and methanol (100 ml) in a Parr hydrogenation apparatus provided 4-(4-chlorophenyl)-3-methoxyaniline (0.4 g) as an oil.

Step C (Compound A)

To a stirred solution of 2-chlorobenzoylisocyanate (0.2 g, 1.1 mmol) in xylenes (40 ml) was added a solution of 4-(4-chlorophenyl)-3-methoxyaniline (0.2 g, 0.9 mmol) in xylenes (ml). The mixture was stirred at ambient temperature for 2.5 hours then diluted with n-heptane (60 ml) and stirred for an additional one-half hour. The resulting precipitate was collected by filtration and washed with cold pentane to provide 2-chloro-N-[{(2-methoxy4'-chloro[1,1'-biphenyl]-4-yl)amino}carbonyl]benzamide, m.p. 178–179° C. (Compound A).

EXAMPLE 2

Compound A and hexaflumuron were evaluated for activity against *Reticulitermes flavipes* as follows. A 0.2 ml solution of compound (Compound A in acetone and hexaflumuron in water) was applied to 4.25 cm filter paper in a 5 cm petri dish and air-dried overnight. Papers were rehydrated with 0.2 ml water and 10 termite nymphs were added to each dish. One drop of water was added to the filter paper as needed (usually every other day) to prevent termite dehydration. The percent control was measured after 30 days of exposure by the termites to the treated filter paper. The results are shown in the Table I.

TABLE I

Relative Activities of Hexaflumuron and Compound A
Against Termite *Reticulitermes flavipes*

| Concentration (w/w %)[b] | Hexaflumuron[a] | Compound A[a] |
|---|---|---|
| 0.01 | 20 | 73 |
| 0.1 | 36 | 90 |
| 1.0 | 100 [c] | 93 [c] |

[a]Percent control after 30 day exposure to treated fliter paper. Average of six replications.
[b]The weight/weight percent of test compound.
[c]90% control was observed within 2–4 days for hexaflumuron and within 22–24 days for Compound A.

EXAMPLE 3

Compound A and hexaflumuron were evaluated for activity against German cockroaches. Baits were prepared as follows: a 5.0 ml solution of compound (Compound A in acetone and hexaflumuron in water) was mixed with 5 g of pulverized Purina Laboratory Rat Chow and air-dried for 24 hours. Ten 3rd instar GCR nymphs were placed in 16 oz.screen-covered plastic tubs with water and harborage. Baits (0.2 g) were added the next day and at two weeks. Percent control was measured after the cockroaches were exposed to the treated diet for 30 days. The results are shown in Table 2.

TABLE 2

Relative Activities of Hexaflumuron and Compound A
Against German Cockroach

| Concentration (w/w %)b | Hexaflumuron[a] | Compound A[a] |
|---|---|---|
| 0.01 | 28 | 50 |
| 0.1 | 65 | 55 |
| 1.0 | 87 | 77 |

[a]Percent control after 30 day exposure to treated diet. Average of six replications.
[b]The weight/weight percent of test compound.

Another embodiment of the present invention relates to a method for controlling domestic pests which comprises applying to the site where control is sought an insecticidally effective amount of a compound of formula I:

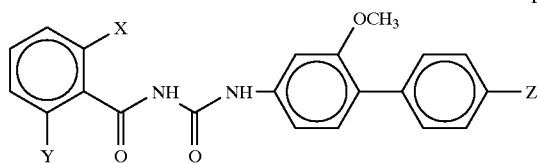

I where X and Y are both fluorine or X is chlorine and Y is hydrogen; and Z is fluorine, chlorine, bromine, alkyl, alkoxy, haloalkyl or haloalkoxy.

The term "alkyl" alone or as part of a larger moiety, includes straight or branched chain alkyl groups of 1 to 6 carbon atoms, while the term "alkoxy" along or as part of a larger moiety, includes straight or branched chain alkoxy groups of 1 to 6 carbon atoms.

TABLE 3

Representative Compounds of Formula I

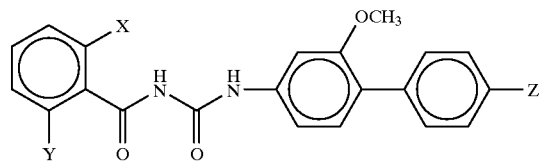

I

| Compound | X | Y | Z |
|---|---|---|---|
| 7 | Cl | H | OCHF$_2$ |
| 8 | Cl | H | OCF$_3$ |
| 9 | Cl | H | CF$_3$ |
| 10 | Cl | H | Br |
| 11 | Cl | H | Cl |
| 12 | Cl | H | CH$_3$ |
| 13 | Cl | H | CH$_2$CH$_3$ |
| 14 | Cl | H | isopropyl |
| 15 | Cl | H | OCH$_3$ |
| 16 | Cl | H | C$_6$H$_{13}$ |
| 17 | Cl | H | F |
| 18 | Cl | H | H |
| 19 | F | F | OCHF$_2$ |
| 20 | F | F | OCF$_3$ |
| 21 | F | F | CF$_3$ |
| 22 | F | F | Br |
| 23 | F | F | Cl |
| 24 | F | F | CH$_3$ |
| 25 | F | F | CH$_2$CH$_3$ |
| 26 | F | F | isopropyl |
| 27 | F | F | OCH$_3$ |
| 28 | F | F | C$_6$H$_{13}$ |
| 29 | F | F | F |
| 30 | F | F | H |

The compounds of formula I may be prepared by the general procedures described above for Compound A. These compounds may be incorporated in a termite bait or composition or other suitable carrier as previously described.

We claim:

1. A method for controlling domestic insect pests selected from the group consisting of termites, cockroaches, fleas, ants and flies which comprises applying to the site where control is sought an insecticidally effective amount of a compound having the formula:

where X and Y are both fluorine or X is chlorine and Y is hydrogen; and Z is fluorine, chlorine, bromine, alkyl, alkoxy, haloalkyl or haloalkoxy.

2. The method of claim 1 wherein said domestic insect pests are termites.

3. The method of claim 1 wherein said domestic insect pests are cockroaches.

4. The method of claim 1 wherein the compound is incorporated in an insect bait.

5. The method of claim 1 wherein the compound is 2-chloro-N-[{(4'-chloro-2-methoxy[1,1'-biphenyl]-4-yl)amino}carbonyl]benzamide.

6. The method of claim 5 wherein said domestic insect pests are selected from the group consisting of termites and cockroaches and wherein said compound is applied at a concentration of about 0.01 wt %.

7. A termiticidal composition comprising a termite bait and a compound having the formula:
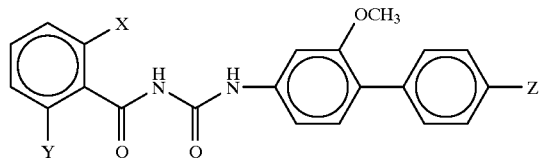
where X and Y are both fluorine or X is chlorine and Y is hydrogen; and Z is fluorine, chlorine, bromine, alkyl, alkoxy, haloalkyl or haloalkoxy.
8. The composition of claim 7 wherein the compound is 2-chloro-N-[{(4'-chloro-2-methoxy[1,1'-biphenyl]4-yl)amino}carbonyl]benzamide.
* * * * *